(12) United States Patent
Yanachkov et al.

(10) Patent No.: US 8,288,545 B2
(45) Date of Patent: Oct. 16, 2012

(54) REACTIVE PYROPHOSPHORIC AND BISPHOSPHONIC ACID DERIVATIVES AND METHODS OF THEIR USE

(75) Inventors: Ivan Yanachkov, Shrewsbury, MA (US); George E. Wright, Worcester, MA (US)

(73) Assignee: GLSynthesis Inc., Worcester, MA (US)

( * ) Notice: Subject to any disclaimer, the term of this patent is extended or adjusted under 35 U.S.C. 154(b) by 532 days.

(21) Appl. No.: 12/374,589

(22) PCT Filed: Jul. 23, 2007

(86) PCT No.: PCT/US2007/016553
§ 371 (c)(1),
(2), (4) Date: May 12, 2009

(87) PCT Pub. No.: WO2008/024169
PCT Pub. Date: Feb. 28, 2008

(65) Prior Publication Data
US 2009/0299048 A1 Dec. 3, 2009

Related U.S. Application Data

(60) Provisional application No. 60/832,395, filed on Jul. 21, 2006, provisional application No. 60/832,449, filed on Jul. 21, 2006.

(51) Int. Cl.
*C07F 9/572* (2006.01)
*C07F 9/58* (2006.01)
(52) U.S. Cl. .......................... 546/21; 548/111
(58) Field of Classification Search .............. 546/21; 548/111
See application file for complete search history.

(56) References Cited

U.S. PATENT DOCUMENTS

| | | | |
|---|---|---|---|
| 5,635,160 A | 6/1997 | Stutts et al. | |
| 5,763,447 A | 6/1998 | Jacobus et al. | |
| 6,326,363 B1 * | 12/2001 | Pohjala et al. | 514/103 |
| 6,765,090 B2 | 7/2004 | Yerxa et al. | |
| 2005/0026864 A1 | 2/2005 | Dixon et al. | |

OTHER PUBLICATIONS

Meisel et al. CAS Accession No. 1990:36011.*
Blackburn et al., "Ap4Aa and Other Dinucleoside Polyphosphates," McLennan, A.G. Ed. CRC Press: Boca Raton, FL, 305-342, 1992.
Blackburn et al. "Chemical Synthesis, Separation, and Identification of Diastereoisomers of $P^1,P^4$-Dithio-5',5'''-Diadenosyl $P^1,P^4$-Tetraphosphate and Its $P^1$, $P^3$-Methylene Analogues," *Tetrahedron Lett.* 31, 4371-4374, 1990.
Chan et al., "$P^1,P^4$-Dithio-$P^2,P^3$-Monochloromethylene Diadenosine 5',5'''-$P^1,P^4$-Tetraphosphate: A Novel Antiplatelet Agent," *Proc. Natl. Acad. Sci. USA* 94:4034-4039, 1997.
Maeda et al., "Formation of ribonucleotide 2',3'-cyclic carbonates during conversion of ribonucleoside 5'-phosphates to diphosphates and triphosphates by the phosphorimidazolidate procedure," *Nucleic Acids Res.* 4:2843-2853, 1977.
McKenna et al., "Synthesis of α-Halogenated Methanediphosphonates," *Phosphorus and Sulfur and the Related Elements* 37:1-12, 1988.
Reiss and Moffatt, "Dismutation Reactions of Nucleoside Polyphosphates. III. The Synthesis of α,ω-Dinucleoside 5'-Polyphosphates," *J. Org. Chem.* 30:3381-3387, 1965.
Tarussova et al., "Phosphate and Halophospahonate Analogs of $P^1$, $P^4$-Bis(5'-Adenosyl)Tetraphosphonate and ATP," *Nucl. Acids Res. Symp. Ser.* 14:287-288, 1984.
Yanachkov et al., "P1,P2-diimidazolyl derivatives of pyrophosphate and bis-phosphonates—synthesis, properties, and use in preparation of dinucleoside tetraphosphates and analogs," *Org. Biomol. Chem.* 9:730-738, 2011.
International Search Report for International (PCT) Patent Application No. PCT/US2007/016553, mailed Jan. 23, 2008.
International Preliminary Report on Patentability for International (PCT) Patent Application No. PCT/US2007/016553, issued Jan. 27, 2009.

* cited by examiner

*Primary Examiner* — Joseph Kosack
(74) *Attorney, Agent, or Firm* — Clark & Elbing LLP; Kristina Bieker-Brady

(57) ABSTRACT

This invention features bis-amides of pyrophosphoric acid and bisphosphonic acids, their preparation, and their use in synthesis of $P^1,P^4$-dinucleoside tetraphosphates, tetraphosphonates, and related compounds.

21 Claims, 9 Drawing Sheets

A
B

REACTIVE PYROPHOSPHORIC AND BISPHOSPHONIC ACID DERIVATIVES AND METHODS OF THEIR USE

CROSS-REFERENCE TO RELATED APPLICATIONS

This application is the National Stage of International Application No. PCT/US2007/016553, filed Jul. 23, 2007, which claims benefit of U.S. Provisional Application Nos. 60/832,449 and 60/832,395, both filed on Jul. 21, 2006, each of which is hereby incorporated by reference.

TECHNICAL FIELD

This invention relates to bis-amides of pyrophosphoric acid and bisphosphonic acids, their preparation, and their use in synthesis of $P^1,P^4$-dinucleoside tetraphosphates, tetraphosphonates, and related compounds.

BACKGROUND OF THE INVENTION

Dinucleoside Tetraphosphates—Pharmacology

Bis-adenosine tetraphosphate ($Ap_4A$, $P^1,P^4$-di(5',5''-adenosine)tetraphosphate, see structure 1) is the most important member of the class of bis-nucleoside polyphosphates. These nucleotides are ubiquitously found in variety of cells, and intracellular compartments, and appear to play important roles as both intra- and extracellular messengers in a variety of signaling events. In particular, they have been implicated in cellular stress response, blood pressure regulation, and insulin and glucose level regulation. Bis-adenosine polyphosphates, and in particular $Ap_4A$, are involved in active inhibition of platelet aggregation by high affinity binding to platelet P2T receptors (Chan, et al., *Proc. Natl. Acad. Sci. USA* 94, 4034-4039, 1997). $Ap_4A$ and its phosphonates, e.g. "$Ap_2CHClp_2A$", and the thio-analog, e.g. "$Ap(S)pCHClpp(S)A$" (see structure 2), have been proposed as possible agents for treatment of arterial thrombosis (Chan et al., op cit.).

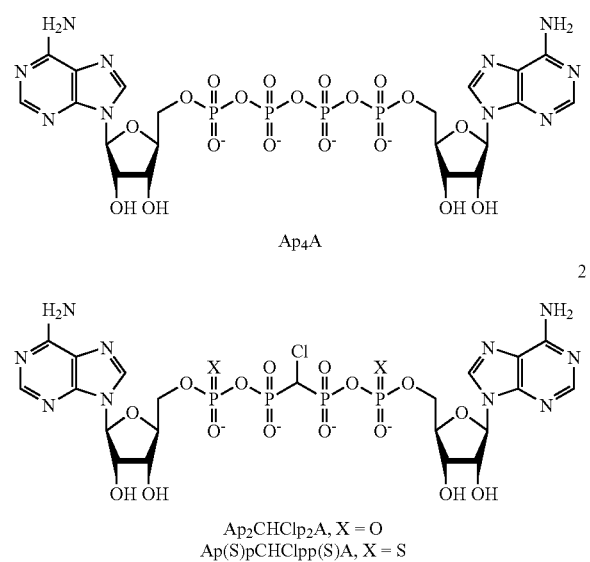

Synthetic dinucleoside tetraphosphates have been studied for other indications, e.g., $Up_4U$ for chronic obstructive pulmonary disease (U.S. Pat. No. 5,635,160) and for prevention and treatment of pneumonia in immobilized patients (U.S. Pat. No. 5,763,447).

Dinucleoside Tetraphosphates—Synthesis

The first synthesis of $Ap_4A$, along with other symmetrical dinucleoside polyphosphates, was reported by the group of Moffatt (*J. Org. Chem.* 30, 3381-3385, 1965) in their classic work on the dismutation of nucleoside polyphosphates. By reaction of 2 equivalents of AMP, activated as the phosphoromorpholidate, with one equivalent of pyrophosphate, Moffatt obtained $Ap_2A$ (8%), $Ap_3A$ (18%), $Ap_4A$ (23%), $Ap_5A$ (4%), along with ATP (7%), adenosine 5'-tetraphosphate ($Ap_4$, 8%), and minor amounts of AMP and ADP.

Reaction of an excess of an activated nucleoside monophosphate with pyrophosphate remains the main synthetic approach to the synthesis of dinucleoside tetraphosphates and their dithio analogs:

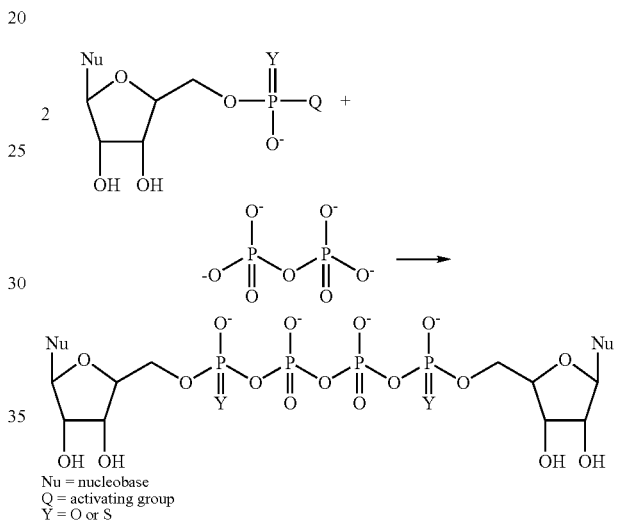

For example Tarussova (*Nucl. Acids Res. Symp. Ser.* 14, 287-288, 1984) used carbonyldiimidazole (CDI) to activate AMP to the imidazolide. Blackburn used diphenylphosphoryl chloride as activating agent for thio-AMP to synthesize, inter alia, $Ap(S)p_2p(S)A$ in 24% yield (*Tetrahedron Lett.* 31, 4371-4374, 1990). In another approach, the AMP, activated as the morpholidate, was reacted with ATP ($Ap_4A$ and *Other Dinucleoside Polyphosphates*; McLennan, A. G. Ed. CRC Press: Boca Raton, Fla., pp 305-342, 1992). Direct catalyzed coupling of nucleoside diphosphates, and reaction of nucleoside triphosphates with nucleoside monophosphates have been reported (U.S. Pat. No. 6,765,090), but in only 10-15% yields.

All of these methods result in formation of considerable amounts of byproducts, such as nucleoside mono, di-, tri-, tetra- and even higher polyphosphates, together with the corresponding dinucleoside di-, tri-, and pentaphosphates. This makes the isolation and purification of the product difficult and time consuming. The chromatographic techniques utilized for that purpose are rarely suitable for large scale preparations.

Dinucleoside Tetraphosphonates—Synthesis

Reaction of an excess of activated nucleoside monophosphate with bisphosphonates remains the main synthetic approach to the synthesis of dinucleoside tetraphosphonates:

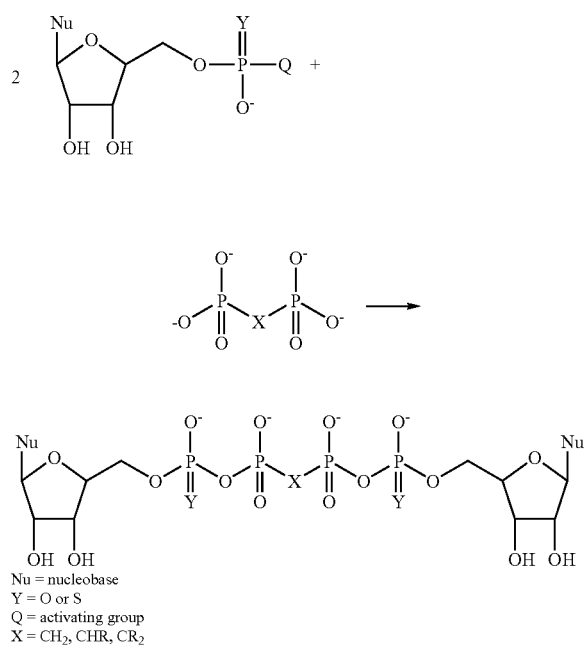

The group of Tarussova (*Nucl. Acids Res. Symp. Ser.* 14, 287-288, 1984) used carbonyldiimidazole (CDI) to activate AMP to the imidazolide, and condensed the imidazolide with methylenediphosphonate to give AppCH$_2$ppA in 30% yield. The group of Blackburn used the Moffatt morpholidate method to prepare the same compound, along with other halomethylene analogs, in yields from 32 to 36% (Blackburn et al., In: *Ap$_4$A and Other Dinucleoside Polyphosphates*; McLennan, A. G. Ed. CRC Press: Boca Raton, Fla., pp 305-342, 1992). They also used diphenylphosphoryl chloride as activating agent for thio-AMP to synthesize Ap(S)pCH$_2$pp(S)A, Ap(S)pCF$_2$pp(S)A, and Ap(S)pCHFp(S)A in yields from 24 to 54% (*Tetrahedron Lett.* 31, 4371-4374, 1990).

Another possible approach is to react activated AMP with ATP analogs. The group of Blackburn used this method to prepare AppCCl$_2$ppA from AppCH$_2$p and AMP morpholidate in 46% yield (*Ap$_4$A and Other Dinucleoside Polyphosphates*, loc cit).

All of these methods result in formation of considerable amounts of byproducts, such as nucleoside mono, di-, tri-, tetra- and even higher polyphosphonates, together with the corresponding dinucleoside di-, tri-, and pentaphosphonates. This makes the isolation and purification of the product difficult and time consuming. The chromatographic techniques utilized for that purpose are rarely suitable for large scale preparations.

The low yields and high cost of preparing potential therapeutic analogs of dinucleoside tetraphosphates and tetraphosphonates and related compounds have hampered further testing and development of this class.

SUMMARY OF THE INVENTION

The invention is based on the discovery that certain symmetrical bis-amides of pyrophosphoric and (methylene)bisphosphonic acids are stable, isolable products, and that they can be converted in high yield into P$^1$,P$^4$-dinucleoside-tetraphosphates and P$^1$,P$^4$—P$^2$,P$^3$-methylenetetraphosphonates.

In one aspect, the invention features compounds of formula Ia:

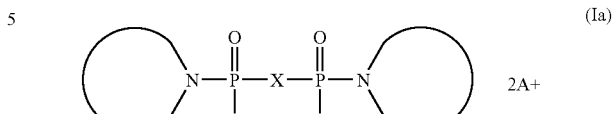

wherein

represents a heterocyclic, nitrogen containing group;
wherein, X is O, CH$_2$, CHY, CY$_2$, C=O, CYZ, where Y and Z are, independently, H, F, Cl, Br, alkyl (C$_{1-6}$), substituted alkyl (C$_{1-6}$, where the substituent, if any, is connected via O, N or S), OR$_1$, NR$_1$R$_2$, where R$_1$ and R$_2$ are, independently, H, alkyl (C$_{1-10}$) optionally substituted, or where Y and Z are connected in the form of a carbocycle (C$_{3-7}$);
and wherein 2A$^+$ is any appropriate counter ion or combination thereof, e.g., an alkali metal (Li$^+$, Na$^+$, K$^+$), a divalent cation (e.g., Ca$^{2+}$, Mg$^{2+}$, or Mn$^{2+}$), ammonium, trialkylammonium (alkyl=C$_{1-8}$), tetraalkylammonium (C$_{1-10}$), imidazolium, or N-alkylimidazolium (C$_{1-6}$).

Alternately, the invention features compounds of formula Ib:

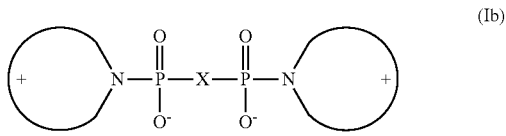

wherein

represents a heterocyclic, nitrogen containing group bearing a permanent positive charge, and X is as defined above.

In one aspect, the invention features compounds of formula IIa:

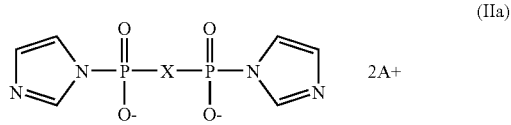

wherein the "heterocyclic, nitrogen containing group" is imidazole, and X is as defined above, and wherein 2A$^+$ is any appropriate counter ion or combination thereof, e.g., an alkali metal (Li$^+$, Na$^+$, K$^+$), a divalent cation (e.g., Ca$^{2+}$, Mg$^{2+}$, or Mn$^{2+}$), ammonium, trialkylammonium (alkyl=C$_{1-8}$), tetraalkylammonium (alkyl=C$_{1-10}$), imidazolium, or N-alkylimidazolium (alkyl=C$_{1-6}$).

In another aspect, the invention features the compounds of formulae IIb and IIc:

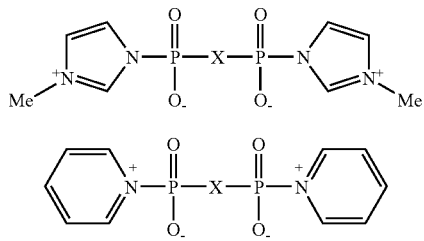

wherein the "heterocyclic, nitrogen containing group" is N-methylimidazole (IIb) or pyridine (IIc), and X is as defined above.

In yet another aspect, the invention features methods of preparing the compounds of formulae Ia, Ib, IIa and IIb involving reacting a salt of pyrophosphoric acid or a bisphosphonic acid with an excess of a carbonyl-bis-(heterocyclic, nitrogen containing group) IIIa or IVa or a carbonyl-(heterocyclic, nitrogen containing group)-trihalomethyl compound) IIIb or IVb, wherein X is F, Cl or Br, and 2A−/A− is any appropriate counteranion (e.g., Cl−) or combination thereof.

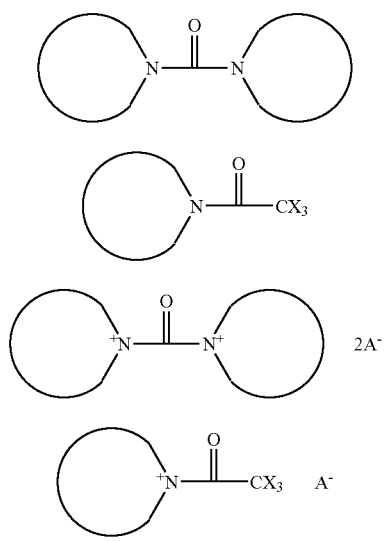

In another aspect, the invention features methods involving combining suitable salts of organic phosphoric acid monoesters or phosphonic acid monoesters or organic thiophosphoric acid monoesters or organic thiophosphonic acid monoesters and the bis-amides of pyrophosphoric or methylenebisphosphonic acids, i.e. compounds of formulae Ia-IIb, in a suitable solvent in such a way as to result in the products of formula V in high yields:

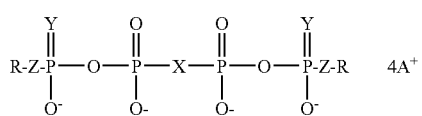

where X and A+ are as defined above, Z is O or $CH_2$, Y is O or S, and where R is a naturally occurring or synthetic organic radical.

In another aspect, the invention features methods involving combining suitable salts of nucleoside monophosphates and a compound of formulae Ia-IIb in a suitable solvent in such a way as to result in $P^1,P^4$-dinucleoside-tetraphosphates or $P^1,P^4$-dinucleoside-$P^2,P^3$-methylene-tetraphosphonates of formula VI:

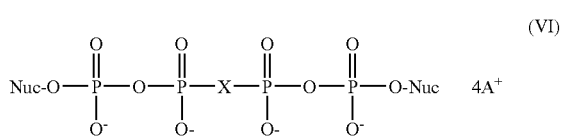

where X and A+ are as defined above, and where Nuc is a nucleoside, nucleotide, or analog thereof, e.g., a natural or synthetic ribonucleosidyl, 2'-deoxyribonucleosidyl radical, Locked Nucleic Acid, peptide nucleic acid, glycerol nucleic acid, morpholino nucleic acid, or threose nucleic acid connected, e.g., via the 5', 3' or 2' carbon of the radical. The nucleotide, nucleoside, or analog may include a purine or pyrimidine moiety, e.g., cytosine, guanine, adenine, thymine, uracil, xanthine, hypoxanthine, inosine, orotate, thioinosine, thiouracil, pseudouracil, 5,6-dihydrouracil, and 5-bromouracil. The purine or pyrimidine may be substituted as in known in the art, e.g., with halogen (i.e., fluoro, bromo, chloro, or iodo), alkyl (e.g., methyl, ethyl, or propyl), acyl (e.g., acetyl), or amine or hydroxyl protecting groups.

In another aspect, the invention features methods involving combining suitable salts of nucleoside thiomonophosphates and a compound of formulae Ia-IIb in a suitable solvent in such a way as to result in $P^1,P^4$-dinucleoside-$P^1,P^4$-dithiotetraphosphates or $P^1,P^4$-dinucleoside-$P^2,P^3$-methylene-$P^1,P^4$-dithiotetraphosphonates of formula VII:

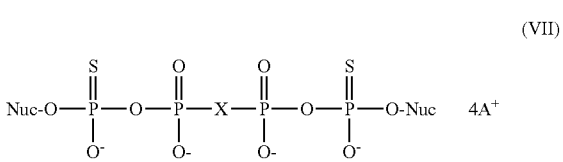

where X, Nuc, and A+ are as defined above:

In yet another aspect, the invention features catalysts that may be used to facilitate methods of preparing the compounds of formulas V, VI and VII, such as 1H-tetrazole, 5-nitro-1H-1,2,3-triazole, imidazolium salts, N-methylimidazolium salts, or divalent metal cations such as $Zn^{+2}$, $Mg^{+2}$ and $Mn^{+2}$.

The invention also features the acid forms of each of the compounds of the invention. For example, compounds of formula Ia or Ib may be singly or doubly protonated. When a compound of formula Ib is single or doubly protonated, an appropriate counteranion or combination thereof may be included. The compounds of formulae V, VI, or VII may be singly, doubly, triply, or four times protonated. In addition, reference to a number of countercharges, e.g., 2A+ or 4A+, includes any single ion or combination of ions to produce a neutral compound. In preferred embodiments, the compounds of formulae Ia, Ib, V, VI, or VII are symmetrical.

By "organic radical" is meant any radical that is attached to another group via a saturated carbon, e.g. $CH_2$, the remainder being any organic moiety. Such organic radicals can represent either naturally occurring molecules or synthetic molecules.

Examples include optionally substituted alkyl groups, alkenyl groups, alkynyl groups, aryl groups, and heterocyclic groups, e.g., nitrogen containing. Other examples include peptides, drugs, lipids, and carbohydrates.

By "heterocyclic, nitrogen containing group" is meant a heterocyclic radical containing one or more rings which may be saturated, unsaturated, or aromatic, wherein at least one ring of the radical contains one or more heteroatoms selected from nitrogen (N), oxygen (O), and sulfur (S) in one or more rings, and where the attachment is through a N. Suitable heterocyclic, nitrogen containing groups for use in the compounds of this invention include radicals of (without limitation) pyrrole, pyrazole, triazole, imidazole, pyrrolidine, pyridine, pyrimidine, morpholine, piperidine, piperazine, oxazole, isoxazole, oxazoline, oxazolidine, oxathiazole, thiazole, isothiazole, thiadiazole, tetrazole, indole, isoindole, quinazoline, quinoline, isoquinoline, purine, pyrrolopyrimidine, pyrazolopyrimidine, and pteridine. In addition, heterocyclic radicals may contain one or more substituents (e.g., a halogen atom, an alkyl radical, or aryl radical) attached to a ring member atom of the heterocyclic radical, such as (without limitation) N-methylimidazole, pyridine, 2-, 3- or 4-picoline, and 2,6-lutidine.

The letter "p" when used in the context of a structure acronym such as $Ap_2CH_2p_2A$ represents either a phosphodiester, i.e., —$OP(O_2)O$—, or a phosphonomonoester, i.e., —$OP(O_2)C$—, group.

The letters "p(S)" when used in the context of a structure acronym such as $Ap(S)pCH_2pp(S)A$ represents either a thiophosphodiester, i.e., —$OP(OS)O$—, or a thiophosphonomonoester, i.e., —$OP(OS)C$—, group.

Im is N-imidazolyl.

The details of one or more embodiments of the invention are set forth in the accompanying description below. Other features, objects, and advantages of the invention will be apparent from the description and from the claims.

DETAILED DESCRIPTION OF THE INVENTION

In our search for a more cost-effective way to prepare $Ap_4A$, $Ap_2CHClp_2A$ and related compounds, we found that pyrophosphoric acid, $O_3P$—O—$PO_3^{-4}$ ("pp"), and chloromethylenebisphosphonic acid, $O_3P$—CHCl—$PO_3^{-4}$ ("pCHClp"), as the tributylammonium salts, reacted with excess carbonyldiimidazole (CDI) to give stable, isolable intermediates found to be the bis-imidazolides of pyrophosphoric and chloromethylenebisphosphonic acids, respectively. These intermediates reacted readily with nucleoside 5'-monophosphates (NMP) to give target compounds $Ap_4A$, $Up_4U$ and $Ap_2CHClp_2A$ in high yields (see, e.g. Scheme 1).

Scheme 1.

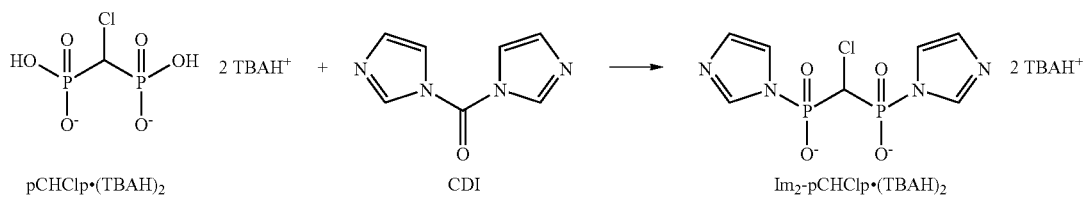

pCHClp•(TBAH)$_2$       CDI       Im$_2$-pCHClp•(TBAH)$_2$

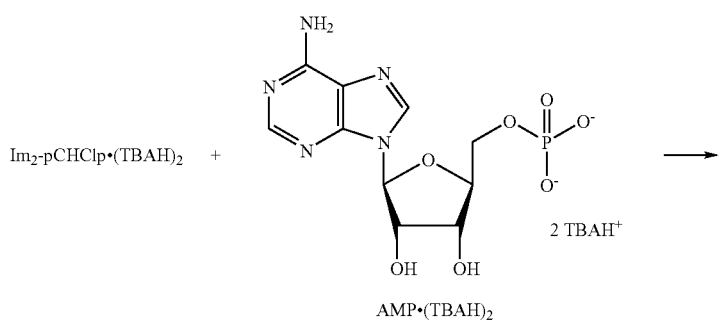

Im$_2$-pCHClp•(TBAH)$_2$   +                                    AMP•(TBAH)$_2$

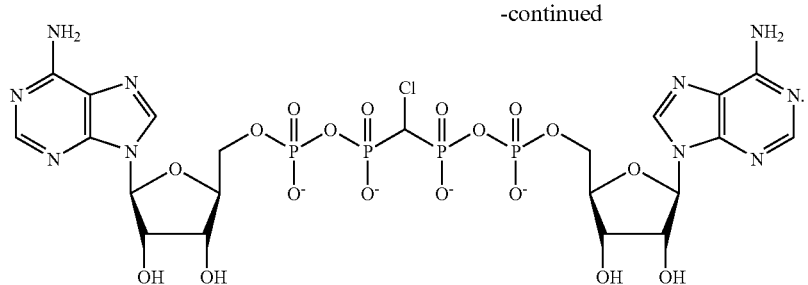

Ap2CHClp2A        4 TBAH⁺ or 4 Na⁺

TBAH = tributylammonium

We have also unexpectedly discovered that bis-amides of pyrophosphoric acid and bisphosphonic acids can be synthesized and isolated in pure form, and that such bis-amides of pyrophosphoric acid and bisphosphonic acids react with organic phosphoric acid monoesters or phosphonic acid monoesters or organic thiophosphoric acid monoesters or organic thiophosphonic acid monoesters to produce valuable tetraphosphate or tetraphosphonate compounds in high yields. When the organic phosphate is a nucleoside 5'-monophosphate or thiomonophosphate, the products so obtained are $P^1,P^4$-bis-(5',5''-nucleosidyl)tetraphosphates and $P^1,P^4$-bis-(5',5''-nucleosidyl)-$P^2,P^3$-methylene-tetraphosphonates, or the corresponding $P^1,P^4$-dithio compounds.

EXAMPLES

All reagents were prepared by published methods or obtained commercially. Methylenebisphosphonic acids were prepared by well known methods (e.g., McKenna, et al. *Phosphorus Sulfur Relat. Elem.* 37, 1-12, 1988).

Example 1

Bis-imidazolylpyrophosphate (ImppIm)

Figure 1A:
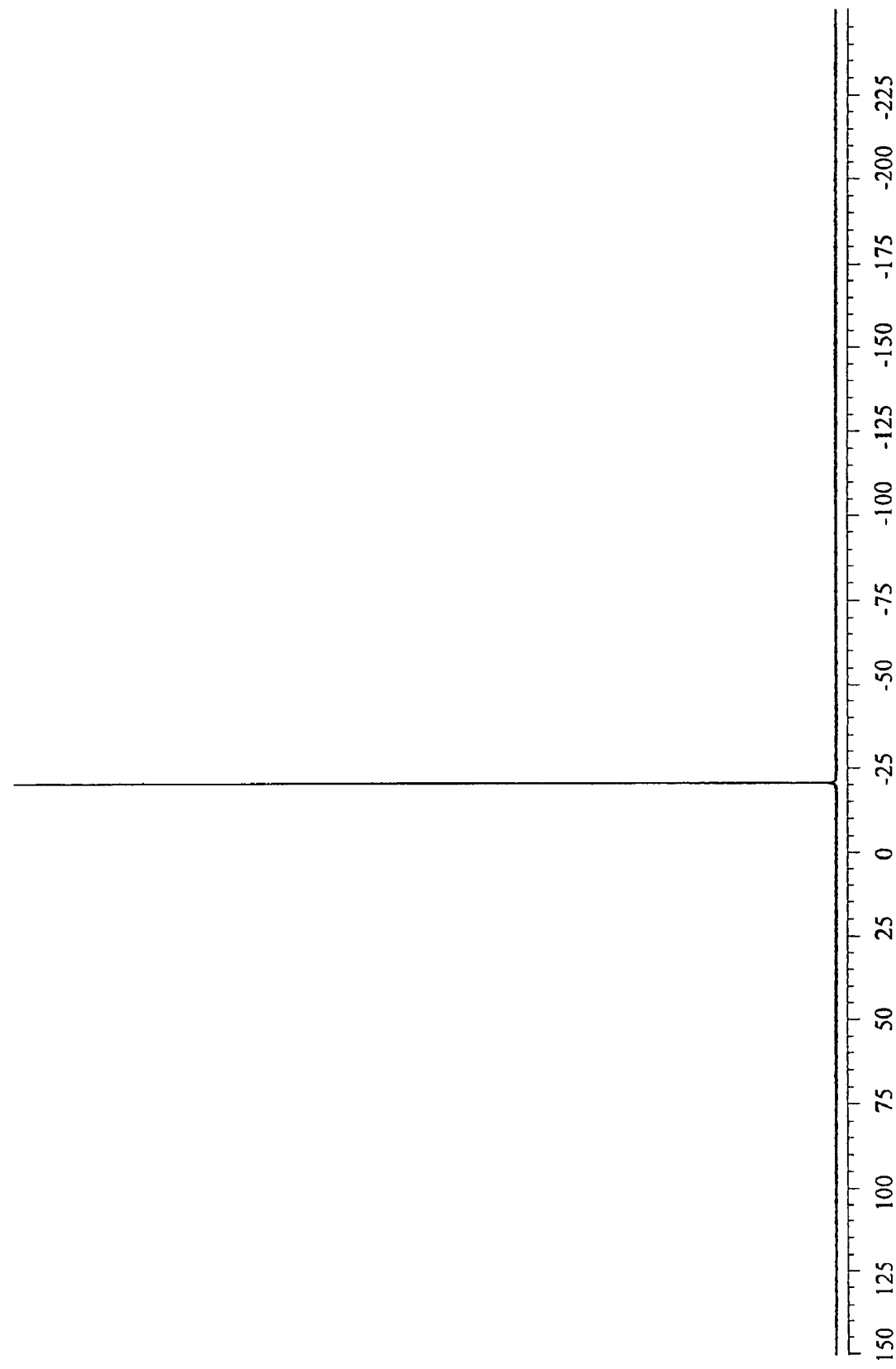
FIG. 1. Bis-(N-imidazolyl)pyrophosphate (ImppIm): $^{31}P$ Spectra of the reaction mixture after 16 hours. A: full spectrum; B: expansion.
Figure 1B:
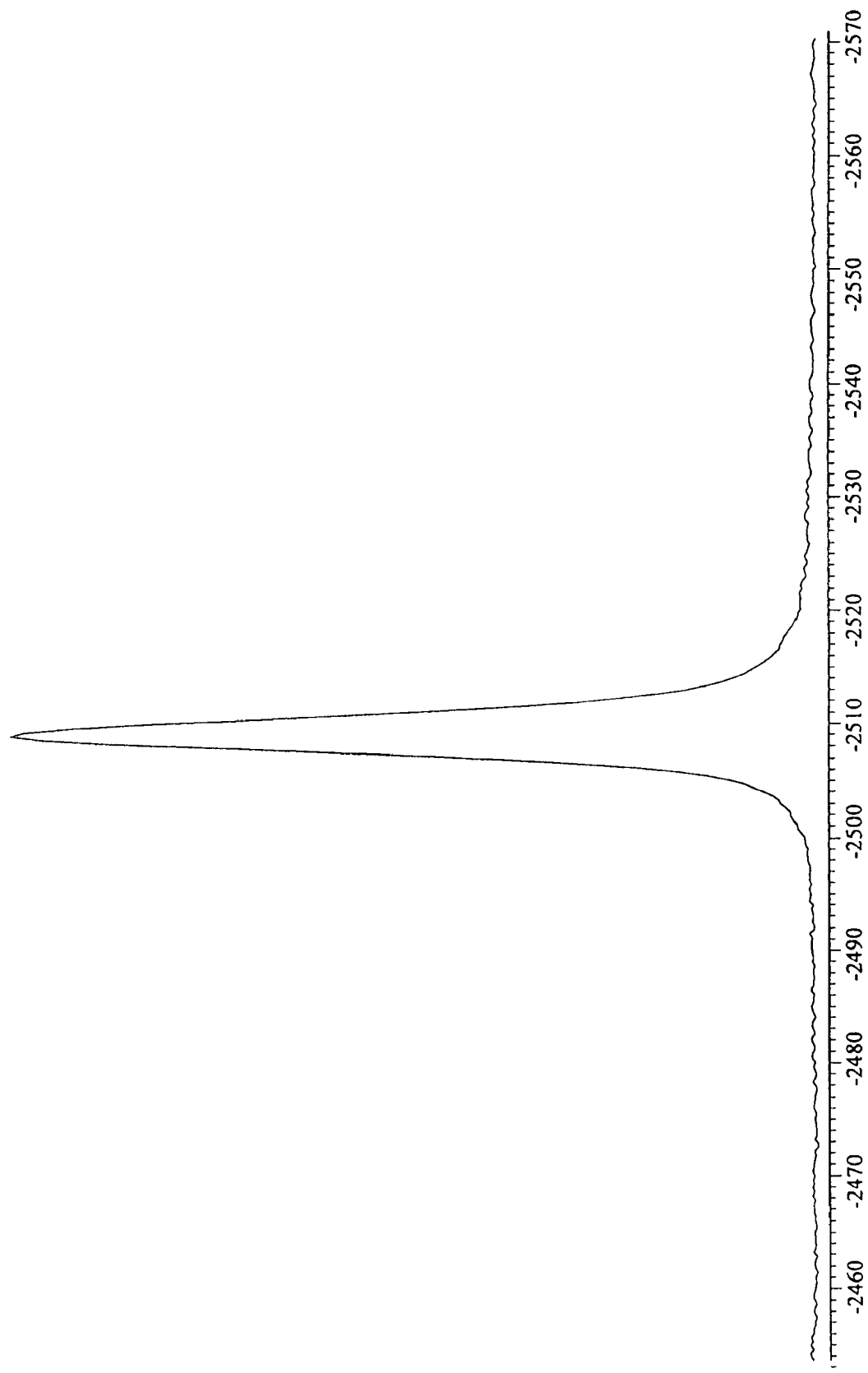

Carbonyldiimidazole (CDI), 2.43 grams (15 mmol), was suspended in 5 ml dry N,N-dimethylformamide (DMF) under an atmosphere of $N_2$. A solution of the bis-tributylammonium salt of pyrophosphoric acid (2.74 grams, 5 mmol) in DMF (3.5 ml) was added with stirring, followed by tributylamine (0.927 grams, 5 mmol, 1.19 ml). Rapid carbon dioxide evolution started, and CDI dissolved quickly. After 16 hours $^{31}P$ NMR (FIG. 1) showed only a signal for ImppIm, and no signals for starting pyrophosphoric acid or byproducts. Water (0.2 ml) was added with stirring to destroy excess CDI. After 5 min the reaction mixture was concentrated under vacuum, and the residue was stored in a freezer at −10° C. until used.

Figure 2:
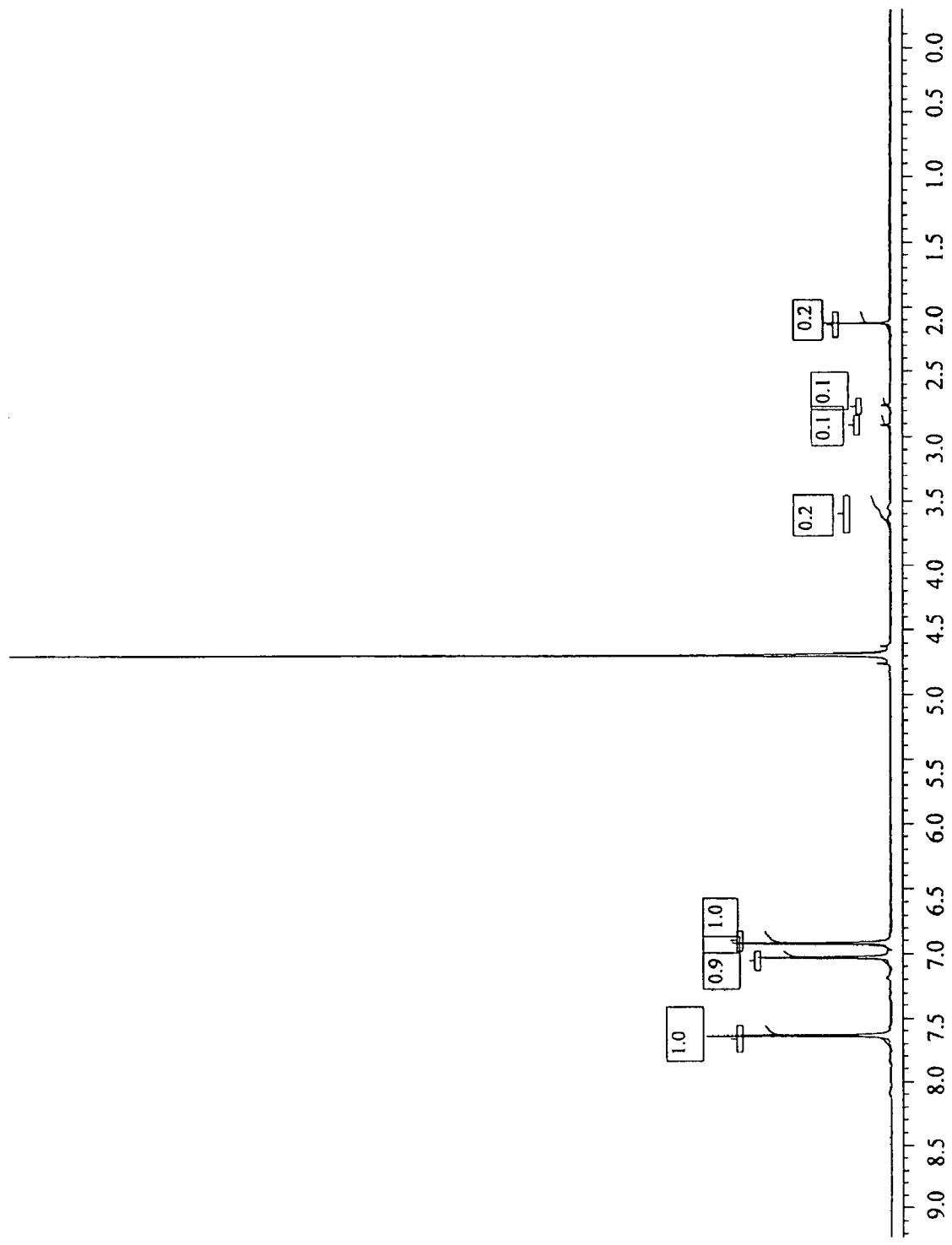
FIG. 2: $^1H$ NMR spectrum of bis-(N-imidazolyl)pyrophosphate, di-Na salt, in $D_2O$.
Figure 3:
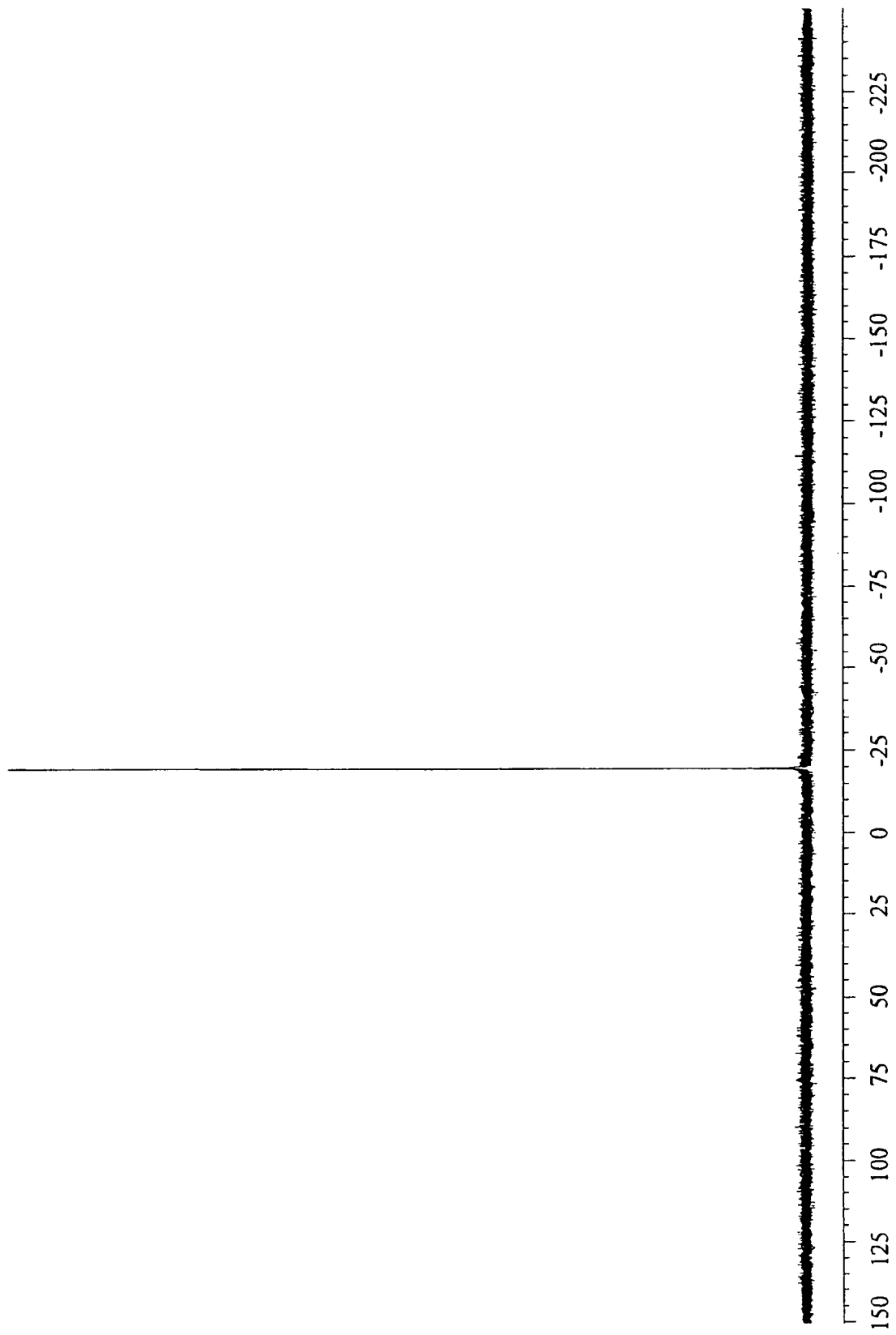
FIG. 3: $^{31}P$ NMR spectrum of bis-(N-imidazolyl)pyrophosphate, di-Na salt, in $D_2O$.
Figure 4:
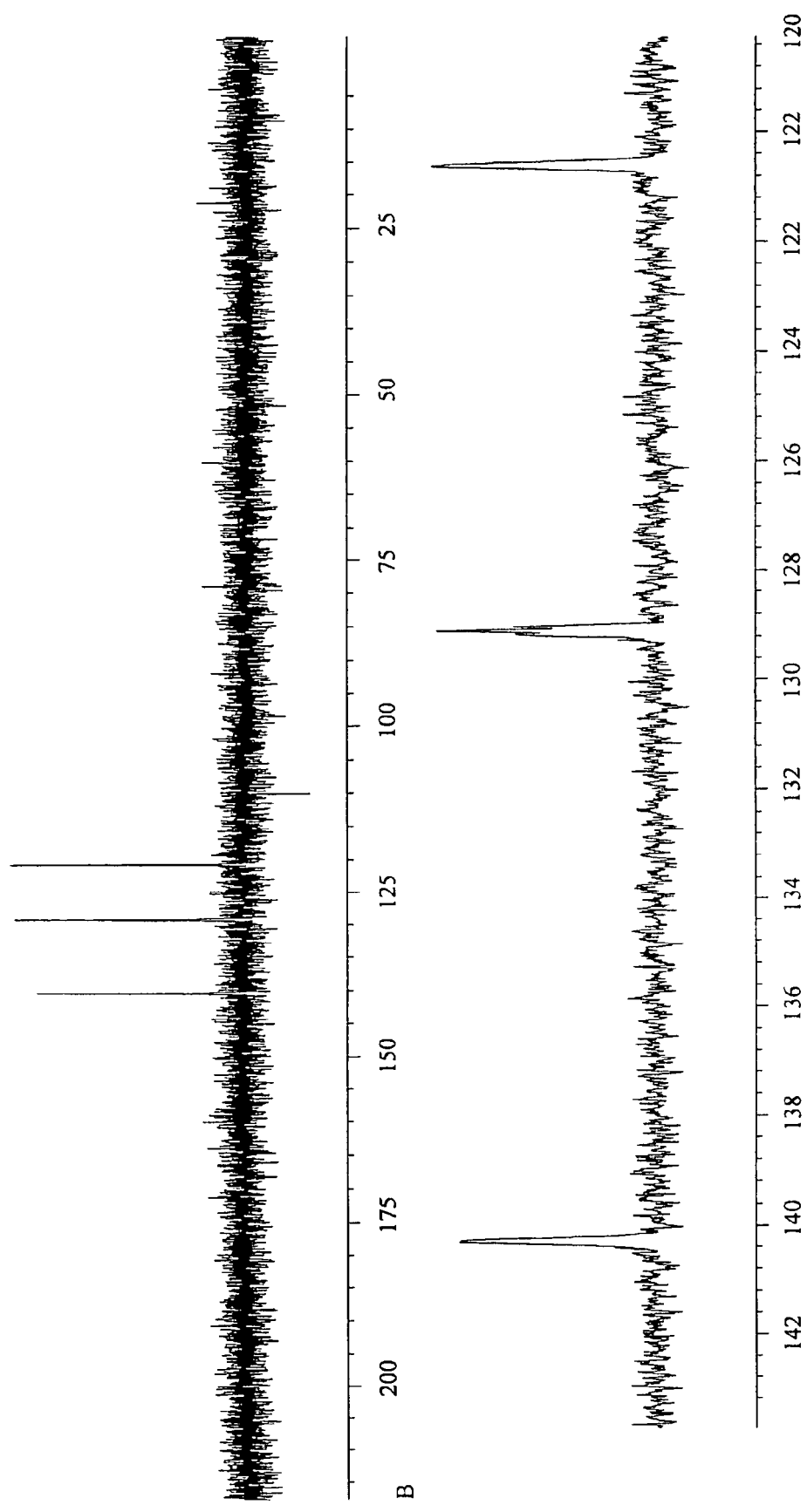
FIG. 4: $^{13}C$ (proton coupled) NMR spectrum of bis-(imidazolyl)pyrophosphate, di-Na salt, in $D_2O$. A: full spectrum; B: expansion.

For preparation of the di-sodium salt of ImppIm, 47 mg of the residue was mixed with 600 μL of 2M sodium perchlorate solution in acetone. The mixture was diluted with 3 ml acetone, which resulted in separation of a gummy residue. After stirring for ½ hour this residue converted to a fine white powder. This powder was separated by centrifugation, the liquid was decanted, and the precipitate was washed twice by resuspension in 3.5 ml acetone, centrifugation, and decanting. The washed precipitate of ImppIm, di-Na salt, was dried in vacuo, and characterized by proton (FIG. 2), phosphorus (FIG. 3), and carbon (FIG. 4) NMR spectra in $D_2O$.

Example 2

Bis-(N-imidazolyl)chloromethylenebisphosphonate, ImpCHClpIm

Figure 5:
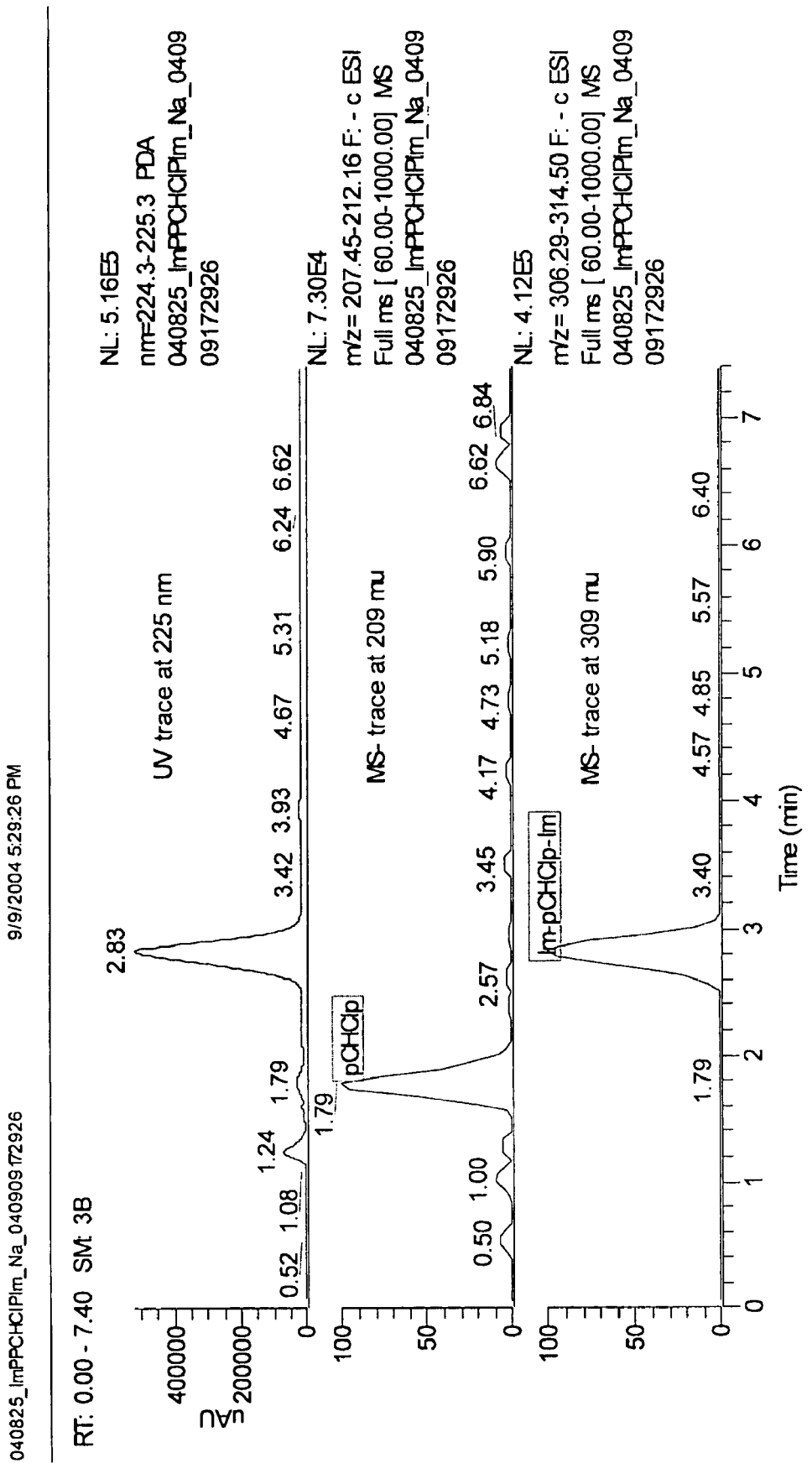
FIG. 5. LC-MS results for reaction of pCHClp with CDI.
Figure 5:
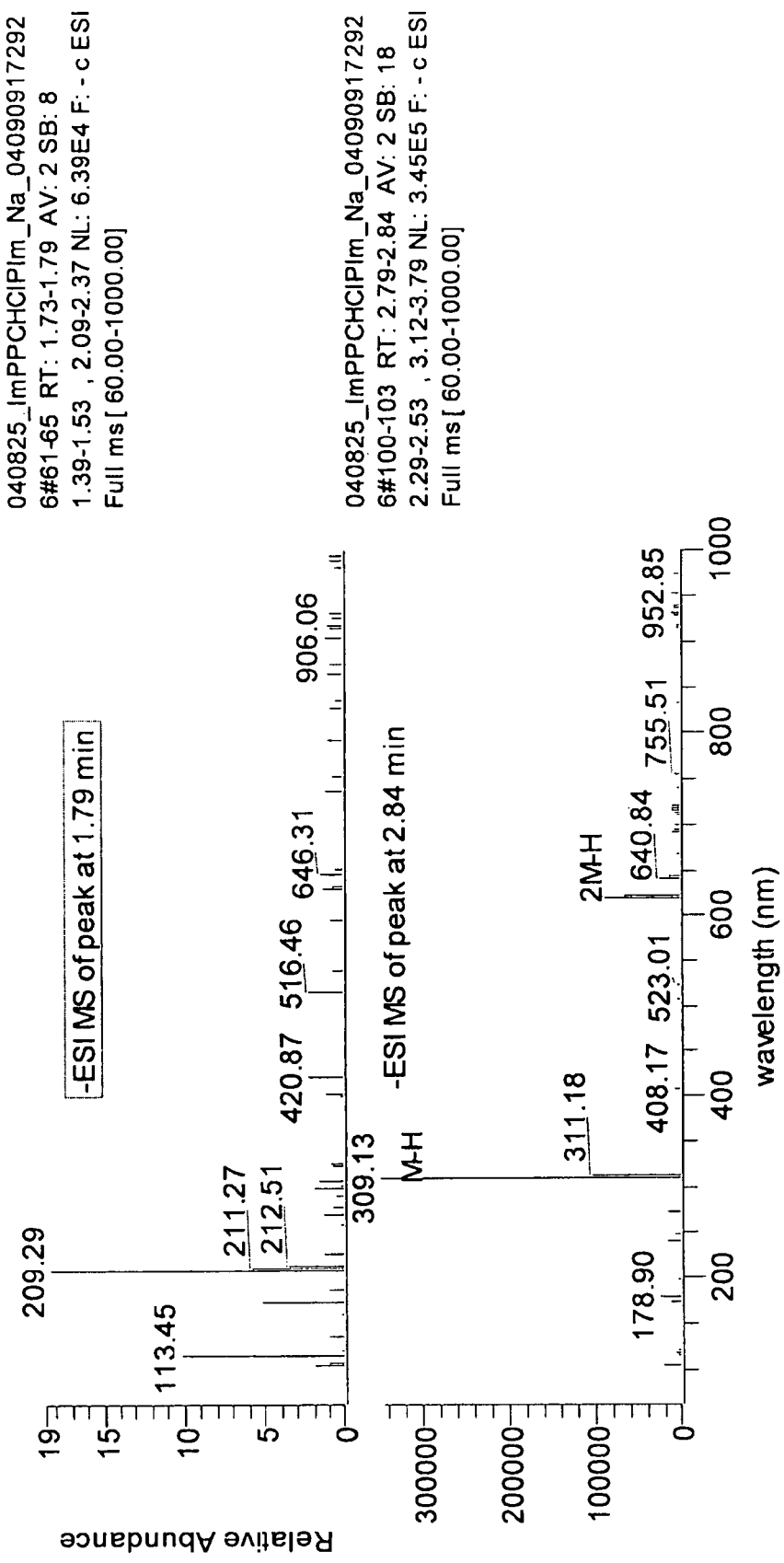
Figure 6:
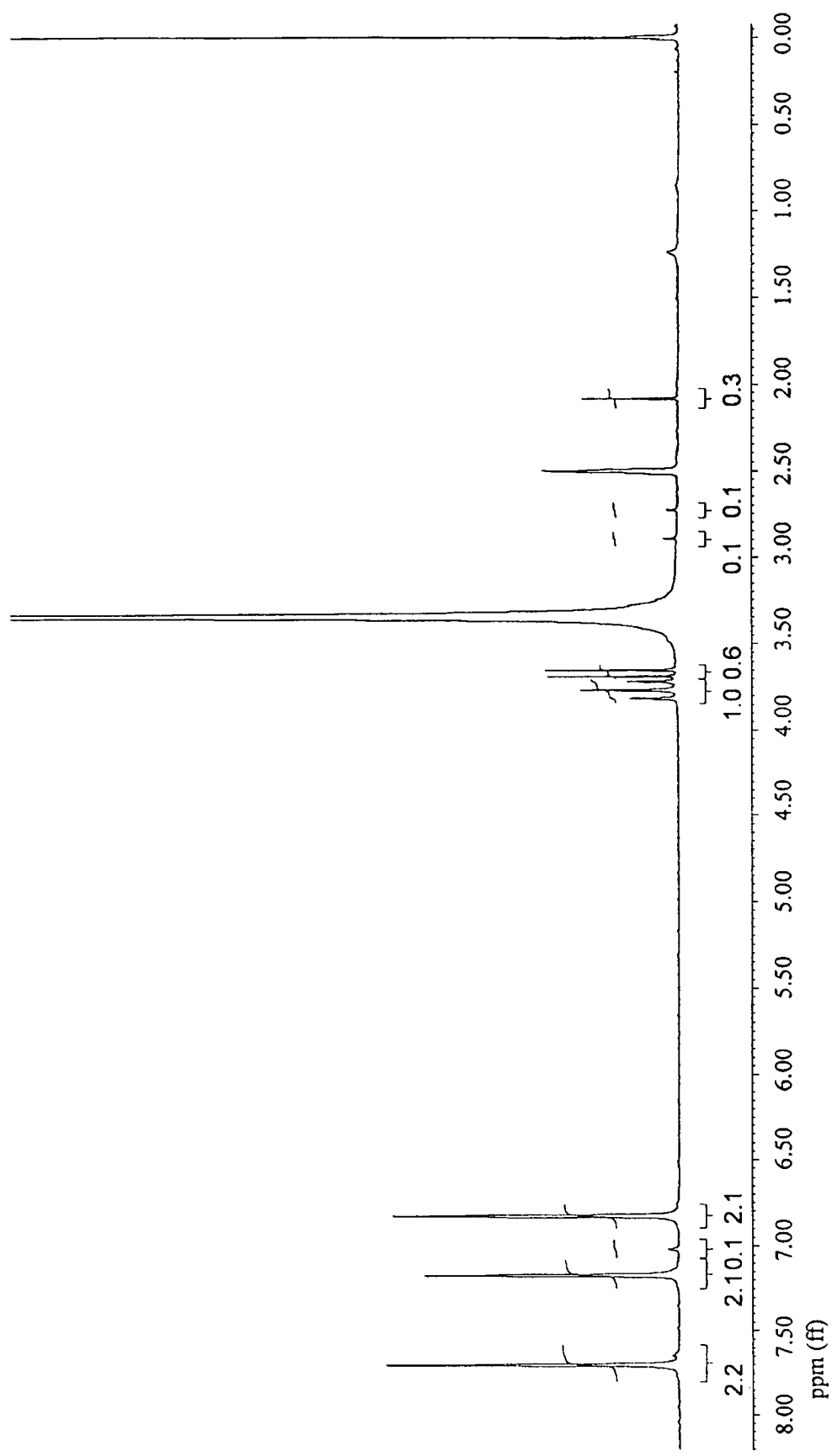
FIG. 6. $^1H$ NMR spectrum of bis-(N-imidazolyl)chloromethylenebisphosphonate, ImpCHClpIm, di-Na salt, in DMSO-$d_6$.
Figure 7:
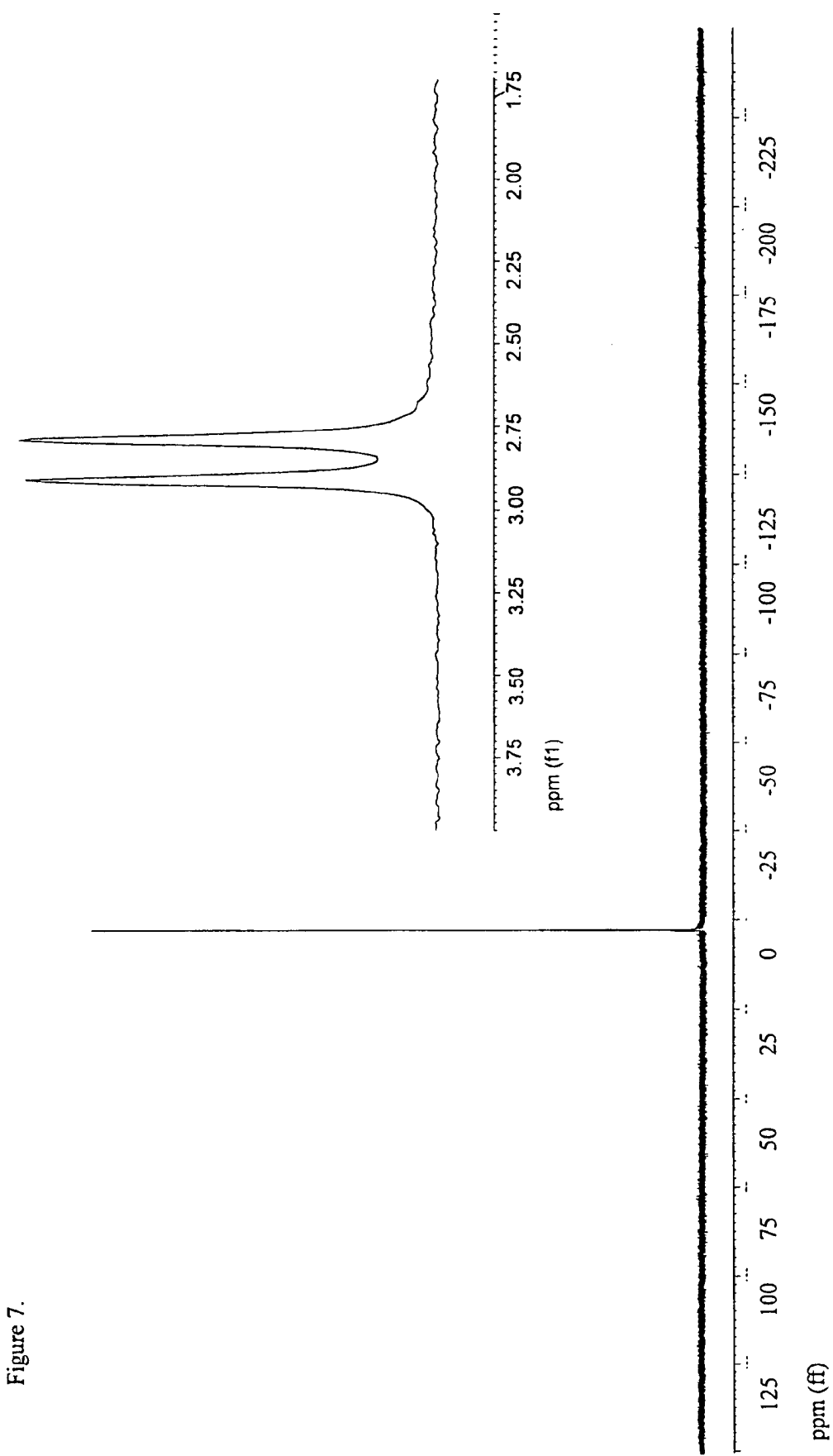
FIG. 7. $^{31}P$ NMR proton-coupled spectrum of ImpCHClpIm, di-Na salt, in DMSO-$d_6$. Insert: expansion.

The bis-imidazolide of chloromethylenebisphosphonic acid (pCHClp) was prepared by reaction of the bis-tributylammonium salt of pCHClp in N,N-dimethylformamide (DMF) with 5 equivalents of carbonyldiimidazole (CDI). The rate of the reaction was monitored by the release of $CO_2$ and by LC-MS, which showed in the negative mode gradual disappearance of the peak for pCHClp (209 mu) and appearance of a new peak with mass of 309 mu, corresponding to the bis-imidazolide (FIG. 5). This product was isolated as the sodium salt by precipitation of the reaction mixture with $NaClO_4$ in acetone, and the white precipitate was filtered under $N_2$, washed with acetone, $Et_2O$, and dried under a steam of Ar and then under high vacuum, to give a quantitative yield of the di-sodium salt of the bis-imidazolide ImpCHClpIm. The $^1H$ and $^{31}P$ NMR spectra (DMSO-$d_6$) are shown in FIGS. 6 and 7.

Example 3

$P^1,P^4$-di(5',5''-uridine)tetraphosphate, $Up_4U$

A solution of CDI (1.62 g, 10 mmol) in anhydrous DMF (8 ml) was mixed with a solution of the bis-tributylammonium salt of pyrophosphoric acid (2 mmol, prepared from 0.892 g of tetrasodium pyrophosphate decahydrate by converting to pyrophosphoric acid with cation exchange resin in H form, neutralizing with two equivalents of tributylamine, and drying by repeated evaporation from DMF under vacuum) in dry DMF (1.5 ml). After stirring for 4 hours, 0.2 ml water were added, and, after 10 minutes, the mixture was concentrated under vacuum, and the residue coevaporated twice from 5 ml of DMF to yield the tributylammonium salt of ImppIm. A solution of UMP mono-(trioctylammonium) salt (8 mmol, prepared from 3.00 g of UMP di-Na salt by conversion to the free acid with cation exchange resin in the H form, neutralization with one equivalent of trioctylamine in methanol, and rendering dry by repeated evaporation from DMF under vacuum) in 15 ml dry DMF was added, and the mixture was concentrated under vacuum. The mixture was stirred at room temperature for 48 hours.

The residue was mixed with 15 ml of 1M triethylammonium bicarbonate buffer, extracted twice with 100 ml diethyl ether, and the water layer was loaded on a column of DEAE Sephadex (7.5×30 cm) equilibrated with 10 mM sodium perchlorate, and eluted with a linear gradient from 10 to 200 mM sodium perchlorate at a flow rate of 50 ml/min. Fractions containing Up$_4$U were pooled and concentrated under vacuum to 10 ml, filtered through 0.45 μm filter, and further concentrated to 5 ml. This residue was diluted slowly with stirring with 200 ml of acetone. The mixture was stirred for 3 hours and filtered under vacuum. The precipitate was washed with acetone and dried overnight in vacuo to give 1.512 g (86% based on pyrophosphoric acid) of Up$_4$U, tetra-Na salt, as white crystals. $^1$H NMR (D$_2$O) δ: 7.75 (d, J=7.9 Hz, 1H), 5.90 (d, J=5.3, 1H), 5.80 (d, J=7.78, 1H), 4.26 (m, 2H), 4.13 (m, 3H). $^{31}$P NMR (D$_2$O) δ: −10.13 (m, P$_1$,P$_4$), −20.73 (m, P$_2$,P$_3$). ESI (−) MS (m/z): 789.27, [M-H]$^-$.

Example 4

Conversion of ImppIm to Ap$_4$A

ImppIm as the tetrabutylammonium salt was converted to Ap$_4$A by reaction with AMP in the presence of 1H-tetrazole as catalyst. The product was isolated in 60% yield.

Example 5

Conversion of ImppIm to Ap(S)p$_2$p(S)A

ImppIm as the tetrabutylammonium salt was converted to the dithio analog Ap(S)p$_2$p(S)A by reaction with AMP(S) in the presence of ZnCl$_2$ as catalyst. The product was isolated in 68% yield.

Example 6

Conversion of ImpCHClpIm to P$^1$,P$^4$-di(5',5")adenosine-P$^2$,P$^3$-chloromethylenetetraphosphonate, Ap$_2$CHClp$_2$A A solution of pCHClp in MeOH was neutralized with 2 equivalents of tributylamine (TBA). After coevaporation from DMF, the residue was dissolved in dry DMF under Ar, and CDI (10 eq.) was added. After 4 hours dry Et$_2$O was added, and the precipitate was centrifuged and washed with dry Et$_2$O. $^{31}$P and $^1$H NMR spectra were consistent with the bis-imidazolide (see example 2) plus excess imidazole, and some tributylammonium cation. The residue was dissolved in a mixture of DMF and MeOH, and a solution of 4 eq. of AMP, as the trioctylammonium salt, in DMF was added. The mixture was concentrated to a slurry under high vacuum, and left under Ar overnight. After ca. 15 h the reaction mixture was analyzed by LC-MS. Peaks consistent with Ap$_2$CHClp$_2$A, AMP and a small amount of Ap$_2$A were found. $^{31}$P NMR showed Ap$_2$CHClp$_2$A and AMP in a ratio ca. 1:1, a small amount of Ap$_2$A, and a small amount of another impurity.

After standard work-up by DEAE-Sephadex chromatography the product, Ap$_2$CHClp$_2$A, was isolated in 71% overall yield (from pCHClp) as the triethylammonium salt. This material was converted by standard methods to the sodium salt, whose $^1$H and $^{31}$P NMR spectra were consistent with published results. The purity was above 96% (HPLC).

Example 7

Bis-(N-imidazolyl)fluoromethylenebisphosphonate, ImpCHFpIm, and its Conversion to P$^1$,P$^4$-di(5',5") adenosine-P$^2$,P$^3$-fluoromethylenetetraphosphonate, Ap$_2$CHCFp$_2$A The tributylammonium salt of fluoromethylenebisphosphonic acid (pCHFp) was converted to the bis-imidazolide, as described in example 1 for pCHClp. The excess of CDI was decomposed by addition of a small amount of methanol, and after ½ hour the reaction mixture was concentrated under vacuum, and the imidazolide was reacted in situ with 4 equivalents of AMP, as the tri-octylammoum salt. After standard work-up and DEAE-Sephadex chromatography, Ap$_2$CHCFp$_2$A was isolated in 76% yield as the triethylammonium salt. The triphosphate AppCHFp, the only by-product, was isolated in 6% yield.

All publications, patent applications, patents, and other documents cited herein are incorporated by reference in their entirety. In case of conflict, the present specification, including definitions, will control. In addition, the materials, methods, and examples are illustrative only and not intended to be limiting.

Other variations and embodiments of the invention described herein will now be apparent to those of ordinary skill in art without departing from the scope of the invention or the spirit of the claims below.

What is claimed is:
1. A compound of formula Ia or Ib:

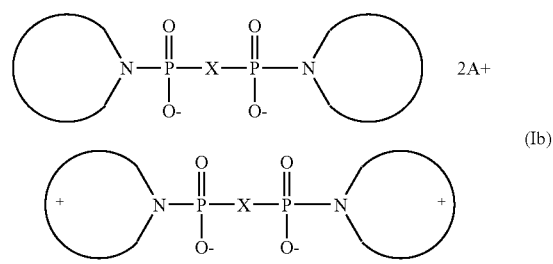

wherein

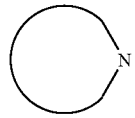

represents a heterocyclic, nitrogen containing group, and wherein

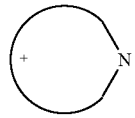

represents a heterocyclic, nitrogen containing group bearing a permanent positive charge;
wherein X is CH$_2$, CHY, CY$_2$, C=O, or CYZ,
where Y and Z are, independently, H; F; Cl; Br; alkyl (C$_{1-6}$); substituted alkyl (C$_{1-6}$), where the substituent is connected via O, N or S; OR$_1$; or NR$_1$R$_2$, where R$_1$ and R$_2$ are, independently, H, alkyl (C$_{1-10}$) optionally substituted; or where Y and Z are connected in the form of a carbocycle (C$_{3-7}$);
and wherein 2A$^+$ is one or more counterions.

2. The compound of claim 1 which is a bis-(N-imidazolyl) bisphosphonate:

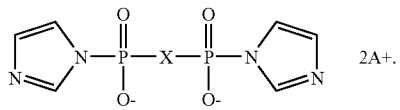

3. The compound of claim 1, wherein X is $CH_2$; CHCl; CHF; $CF_2$; or $CCl_2$.

4. A compound of formula:

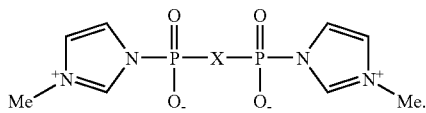

wherein X is O, $CH_1$, CHY, $CY_2$, C=O, or CYZ,
where Y and Z are, independently, H; F; Cl; Br; alkyl $(C_{1-6})$; substituted alkyl $(C_{1-6})$, where the substituent is connected via O, N or S; $OR_1$; or $NR_1R_2$, where $R_1$ and $R_2$ are, independently, H, alkyl $(C_{1-10})$ optionally substituted; or where Y and Z are connected in the form of a carbocycle $(C_{3-7})$.

5. The compound of claim 1 which is a bis-(N-pyridinyl) bisphosphonate:

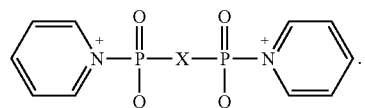

6. The compound of claim 1, wherein X is $CH_2$, CHY, $CY_2$, CYZ, and $A^+$ is an alkali metal cation, ammonium cation, $C_{1-8}$ trialkylammonium cation, $C_{1-10}$ tetraalkylammonium cation, imidazolium cation, or $C_{1-6}$ N-alkylimidazolium cation.

7. A method for synthesizing a compound of claim 1 comprising treating a salt of an appropriate bisphosphonic acid with an excess of a carbonyl bis derivative of a heterocyclic, nitrogen containing compound or a carbonyl, trihaloacetyl heterocyclic, nitrogen containing compound, thereby synthesizing the compound of claim 1.

8. A method for synthesizing a compound of claim 2 comprising treating a salt of an appropriate bisphosphonic acid with excess carbonyldiimidazole, or N-trifluoroacetylimidazole, thereby synthesizing the compound of claim 2.

9. A method for synthesizing a $P^1,P^4$—$P^2,P^3$-methylenetetraphosphonates of formula VI:

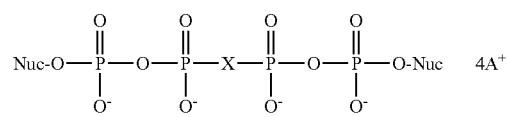

where X is $CH_2$, CHY, $CY_2$, C=O, or CYZ and $4A^+$ is one or more counterions, and where Nuc is a nucleoside, nucleotide, or analog thereof, said method comprising combining a suitable salt of a Nuc-monophosphate and a compound of claim 1, in a suitable solvent thereby synthesizing the $P^1,P^4$—$P^2,P^3$-methylenetetraphosphonate.

10. The method of claim 9, wherein the compound of formula VI is $P^1,P^4$-di(5',5")adenosine-$P^2,P^3$-chloromethylenetetraphosphonate; $P^1,P^4$-di(5',5")adenosine-$P^2,P^3$-fluoromethylenetetraphosphonate; or $P^1,P^4$-di(5',5")uridine $P^2,P^3$-methylenetetraphosphonate.

11. The method of claim 9, wherein Nuc is a natural or synthetic ribonucleosidyl or 2'-deoxyribonucleosidyl radical connected via the 5', 3' or 2' carbon of the radical.

12. A method for synthesizing a compound of claim 1 comprising treating a salt of an appropriate bisphosphonic acid with an excess of a carbonyl derivative of a heterocyclic, nitrogen containing compound in the presence of a catalyst selected from the group consisting of 1H-tetrazole, 5-nitro-1H-1,2,3-triazole, an imidazolium salt, a N-methylimidazolium salt, or a divalent metal cation.

13. A method for synthesizing a $P^1,P^4$-dithio-$P^2,P^3$-methylenetetraphosphonate of formula VII:

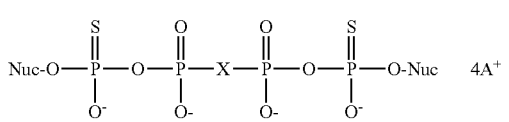

where X is $CH_2$, CHY, $CY_2$, C=O, or CYZ and $4A^+$ is one or more counterions, and where Nuc is a nucleoside, nucleotide, or analog thereof, said method comprising combining an appropriate salt of a Nuc-thiomonophosphate and a compound of claim 1, in a suitable solvent thereby synthesizing the $P^2,P^3$-methylene-$P^1,P^4$-dithiotetraphosphonate.

14. The method of claim 13, wherein the compound of formula VII is $P^1,P^4$-di(5',5")adenosine-$P^2,P^3$-chloromethylene-$P^1,P^4$-dithiotetraphosphonate; $P^1,P^4$-di(5',5")adenosine-$P^2,P^3$-fluoromethylene-$P^1,P^4$-dithiotetraphosphonate; or $P^1,P^4$-di(5',5")uridine-$P^2,P^3$-methylene-$P^1,P^4$-dithiotetraphosphonate.

15. The method of claim 13, wherein Nuc is a natural or synthetic ribonucleosidyl or 2'-deoxyribonucleosidyl radical connected via the 5', 3' or 2' carbon of the radical.

16. A method for synthesizing a compound of formula V:

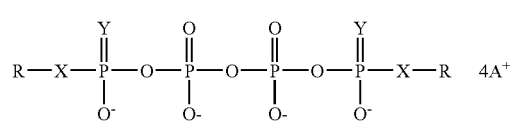

where $4A^+$ is one or more counterions, X is O or $CH_2$, Y is O or S, and where R is a naturally occurring or synthetic organic radical, said method comprising combining a suitable salt of an appropriate organic phosphoric acid monoester, phosphonic acid monoester, or organic thiophosphoric acid monoester or organic thiophosphonic acid monoester with an appropriate compound of claim 9 in a suitable solvent, thereby synthesizing the compound of formula V.

17. The method of claim 16, wherein the compound is bis-[N—(N'-methyl)imidazolyl]pyrophosphate.

18. The method of claim 16, wherein the compound of formula V is $P^1,P^4$-di(5',5"-uridine)tetraphosphate; $P^1,P^4$-di(5',5"-adenosine)tetraphosphate; $P^1,P^4$-di(5',5"-uridine)-$P^1,P^4$-dithiotetraphosphate; or $P^1,P^4$-di(5',5"-adenosine)-$P^1,P^4$-dithiotetraphosphate.

19. The compound of claim 2, wherein X is $CH_2$; CHCl; CHF; $CF_2$; or $CCl_2$.

20. A method for synthesizing a $P^1,P^4$-dinucleoside-tetraphosphate or $P^1,P^4$—$P^2,P^3$-methylenetetraphosphonates of formula VI:

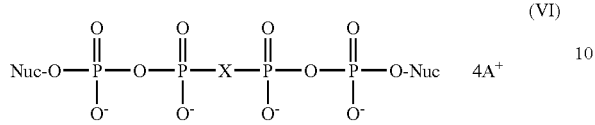

(VI)

where X is O, $CH_2$, CHY, $CY_2$, C=O, or CYZ and $4A^+$ is one or more counterions, and where Nuc is a nucleoside, nucleotide, or analog thereof, said method comprising combining a suitable salt of a Nuc-monophosphate and a compound of claim 9, in a suitable solvent thereby synthesizing the $P^1,P^4$-dinucleoside-tetraphosphate or $P^1,P^4$—$P^2,P^3$-methylenetetraphosphonate.

21. A method for synthesizing a $P^1,P^4$-dinucleoside-$P^1,P^4$-dithiotetraphosphate or $P^1,P^4$-dithio-$P^2,P^3$-methylenetetraphosphonate of formula VII:

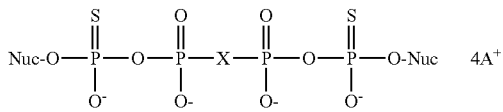

(VII)

where X is O, $CH_2$, CHY, $CY_2$, C=O, or CYZ and $4A^+$ is one or more counterions, and where Nuc is a nucleoside, nucleotide, or analog thereof, said method comprising combining an appropriate salt of a Nuc-thiomonophosphate and a compound of claim 9, in a suitable solvent thereby synthesizing the $P^1,P^4$-dinucleoside-$P^1,P^4$-dithiotetraphosphate or $P^2,P^3$-methylene-$P^1,P^4$-dithiotetraphosphonate.

* * * * *